United States Patent [19]
Ring et al.

[11] Patent Number: 5,294,448
[45] Date of Patent: Mar. 15, 1994

[54] DELAYED RELEASE FORMULATIONS

[75] Inventors: Stephen G. Ring; David B. Archer, both of Norwich; Michael C. Allwood, Derby; John M. Newton, London, all of England

[73] Assignee: British Technology Group Limited, London, England

[21] Appl. No.: 867,696

[22] PCT Filed: Nov. 22, 1990

[86] PCT No.: PCT/GB90/01803
§ 371 Date: Jul. 7, 1992
§ 102(e) Date: Jul. 7, 1992

[87] PCT Pub. No.: WO91/07949
PCT Pub. Date: Jun. 13, 1991

[30] Foreign Application Priority Data

Nov. 24, 1989 [GB] United Kingdom ............... 8926639

[51] Int. Cl.$^5$ .................... A61K 9/32; A61K 9/36; A61K 9/58; A61K 9/62
[52] U.S. Cl. .................... 424/497; 424/475; 424/479; 424/480; 424/482; 424/493; 424/495

[58] Field of Search ............ 424/495, 493, 497, 490, 424/475, 479, 480, 482

[56] References Cited

U.S. PATENT DOCUMENTS 4,642,111 2/1987 Sakamoto et al. .................. 604/890
5,108,758 4/1992 Allwood et al. .................... 424/489

FOREIGN PATENT DOCUMENTS 0343993 11/1989 European Pat. Off. .

OTHER PUBLICATIONS

Chemical Abstracts vol. 112, No. 4, 1989 #25512n.
Chemical Abstracts vol. 109, No. 23, 1988 #206669c.

*Primary Examiner*—Thurman K. Page
*Assistant Examiner*—James M. Spear
*Attorney, Agent, or Firm*—Nixon & Vanderhye

[57] ABSTRACT

Delayed release compositions comprising an active compound and amorphous amylose and having an outer coating comprising a film forming cellulose or acrylic polymer material, for example glassy amylose are of particular value for the selective release of medicaments and diagnostic agents into the colon.

12 Claims, No Drawings

DELAYED RELEASE FORMULATIONS

The present invention relates to delayed release formulations, especially those in which the delayed release characteristic is due to a coating. The term "coating" is used herein to encompass coatings for solid supports and also capsules enclosing fluids and/or solids and the term "coated" is used similarly.

In many situations it is desirable to coat an active substance in such a way that the active substance is released from the coating only after a predetermined interval or only after a change in environment. In a medical context, it is particularly advantageous to be able to administer orally a medicament which is coated so that it passes through the stomach and is released only when the coated material reaches the small intestine. Such coatings are called "enteric" coatings and are relatively easy to formulate taking advantage of the fact that the stomach contents are acid and the intestinal contents are neutral to slightly alkaline.

A harder task has been to provide a coated medicament which will survive both the stomach and the small intestine and will release the active ingredient only when the material reaches the large intestine or colon.

Many diseases of the colon, for example ulcerative colitis and Crohn's disease and potentially also cancer of the colon, could be better treated if site-specific delivery of the therapeutic agent could be effected. Therapeutic agents include corticosteroids, for example hydrocortisone and prednisolone, bisocodyl, phenolphthalein, rhein, sulphasalazine, cholestyramine, azathioprine, 5-aminosalicylic acid and various antibiotics and smooth muscle relaxants. Few effective oral therapies are available, and administration via the rectum is messy and relatively expensive. If drugs for the treatment of colonic disease are encapsulated in an enteric coating, absorption of the drug from the small intestine is very rapid, and only small amounts of the drug reach the required site of action. If site-specific release could be obtained, smaller doses would be required, with a reduction in undesirable side effects.

There are also situations other than the treatment of diseases of the colon where it is desirable to deliver a drug to the colon before it is released. Thus, in certain conditions such as arthritis the release of drugs in the ileum can cause problems and it is desirable for laxatives and anti-diarrhoeal drugs to be selectively released in the colon. Other drugs may also benefit from such a form of release depending upon their absorption characteristics.

A number of approaches have been suggested for site-specific release to the colon. Thus, glycoside derivatives of steroid drugs are reported to be poorly absorbed in the stomach and small intestine but to be released in the large intestine through microbial action (Friend, D. R. and Chang, G. W., J. Med. Chem., 1984, 27, 261). Moreover, coating of peptide drugs with polymers cross-linked with azoaromatic groups is reported to protect the drugs from digestion in the stomach and small intestine but allow their release in the large intestine by the action of the indigenous microflora to effect reduction of the azo bonds (Saffron, M. et al., Science, 1986, 233, 1081).

In U.K. Patent Application No. 8912048.9 (published as GB 2220350A) the use of glassy amylose is described for the purpose of effecting site-specific release in the colon. That application does refer to the possibility of further coating an amylose coated compound but only in the context of the use of "a conventional gelatin or enteric coating" for this purpose. It has now been found that especially advantageous results may be obtained using a particular form of additional coating material in conjunction with glassy amylose or even with the other predominantly amorphous form of amylose, rubbery amylose.

According to the present invention a delayed release composition comprises an active compound and amorphous amylose and has an outer coating comprising a film forming cellulose or acrylic polymer material.

The invention is based on the finding that providing an outer coating comprising cellulose or acrylic polymer material enhances the release characteristics of the composition. Without commitment to any particular mode of action of delayed release for the compositions of the present invention when administered orally in vivo it is believed that the cellulose or acrylic polymer material functions in the stomach and small intestine to support the role played by the amylose in preventing release of the active compound in those parts of the digestive system. However, the cellulose or acrylic polymer material is believed gradually to be weakened as the composition passes through the digestive system so that when it reaches the colon release of the active compound therein is governed substantially by the breakdown of the amylose through the action of enzymes deriving from the microflora present in the colon.

The film forming cellulose materials used in the compositions of the present invention may be of various forms but are preferably cellulose ethers including sodium carboxymethyl cellulose, sodium carboxymethyl 1-hydroxyethyl cellulose, 2-hydroxyethyl cellulose, 2-hydroxypropyl cellulose, methyl cellulose, 2-hydroxyethyl methyl cellulose, 2-hydroxypropyl methyl cellulose, 2-hydroxybutyl methyl cellulose and 2-hydroxyethyl ethyl cellulose, which are classed as water-soluble, and particularly 2-cyanoethyl cellulose, ethyl 2-hydroxyethyl cellulose and especially ethyl cellulose, which are classed as organic solvent-soluble. Mixtures of the different celluloses may be used.

Although the cellulose materials are the preferred film forming materials for use as the outer coating, acrylic polymer materials may also be employed in the compositions of the present invention either alone or in admixture with a cellulose material. In particular, both acrylate and methacrylate polymers may be used and especially copolymers thereof, the esterifying groups in these polymers being of various types, for example of $C_1$-$C_{18}$ alkyl groups.

A preferred molecular weight range for the film forming cellulose materials is 42,000 to 280,000 g/mol (or daltons) and for the film forming acrylic polymer materials is 150,000 to 250,000 g/mol (or daltons) but materials with molecular weights outside these ranges, for example of a higher molecular weight, can be used where appropriate.

The degradation of the cellulose materials in vivo is in general not pH dependent and it is preferred that this is also true for the acrylate materials. This may be achieved by the selection of appropriate forms of side chain on the main polymer chain, in particular of side chains which have a low negative charge or preferably which are uncharged, as opposed to those having a positive charge. Preferred forms of acrylate materials are those marketed by Dumas (UK) Limited of Tunbridge Wells under the Trade Mark Eudragit, particularly the materials Eudragit RL and RS whose degradation is independent of pH. The preferred cellulose material, ethyl cellulose, is marketed by the Dow Chemical Company and Shinetsu Chemical Products under the Trade Mark Ethocel.

As indicated, glassy amylose is one of the two forms of predominantly amorphous amylose, the other being a rubbery form, and it is glassy amylose which is the amylose of choice for use in this invention. Amylose exists in its glassy state below the glass transition temperature (Tg). Rising through this temperature, there is a sharp increase in the heat capacity of the amylose of $0.5 \pm 0.15$ $Jg^{-1}K^{-1}$ (joules per gram per degree Kelvin). This heat capacity increment allows the Tg to be identified and can be measured by differential scanning calorimetry. (Examples of procedures for obtaining Tg values and earlier literature references to such procedures are given in Orford et al, Int. J. Biol. Macromol., 1989, 11, 91.)

The particular Tg of a given preparation of amylose depends upon its purity and other properties. Thus, for example, the theoretical Tg for pure, dry amylose may be predicted to be 210° C. but the presence of water depresses this figure: with 10% w/w of water the Tg is 80° C. and at 20% w/w of water it is 7° C. It has been found that $\alpha$-amylolytic enzymes do not readily degrade glassy amylose and this effect is still apparent at up to 20° C. above the Tg. Such materials have been found to be sufficiently insoluble in aqueous media over the pH range 1-9 at 37° C. to be resistant to degradation in the stomach or intestine. They are, however, degraded by faecal micro-organisms present in the colon. As indicated, the ability of glassy amylose to provide the required delayed release characteristics is not lost immediately the glassy amylose passes through the Tg and amylose which has been produced in the glassy condition at temperatures less than the Tg may therefore then be utilised at the Tg or at temperatures slightly higher than the Tg as well as at temperatures less than the Tg, whilst still retaining its glassy properties. However, the glassy amylose used in the present invention preferably has a Tg of no less than 20° C. below the temperature at which use of the composition is envisaged, i.e. at body temperature of about 37° C. Thus the Tg of the amylose will conveniently be not more than 20° C. below 37° C. i.e. more than or equal to 17° C., and is preferably more than or equal to about 30° C. or, more preferably, more than or equal to about 40° C. The Tg can be predetermined by controlling the amount of water in it. This can be achieved by varying the concentration of the amylose solution which is cooled or sprayed, and by drying the resulting gel.

The ultimate test of the suitability of a particular sample of amylose under any given conditions is of course its ability to resist hydrolytic degradation under aqueous conditions, particularly at a pH of 1-9 and a temperature of 37° C., and conveniently also to resist enzymatic degradation in the presence of the digestive enzymes such as normally occur in the stomach and the small intestine, but to undergo enzymatic degradation in the presence of amylose-cleaving enzymes such as are provided by the microbial flora normally present in the large intestine (see tests described in Examples 1 and 4).

The amylose may conveniently be prepared in a glassy form either by forming a gel from an aqueous solution and then drying it or by spray drying. In the former process, the solution is conveniently 1.5–40% w/w amylose, preferably 3 to 30%, more preferably 4 to 20% and most preferably 6 to 10%, and is conveniently cooled from 70°–95° C., preferably 88°–92° C., to 0° to 40° C., preferably 5° to 35° C., most preferably 10° to 30° C., at a rate of $10^{-3}$ to $10^5$ °C./second, preferably 0.1 to 1.0 °C./second. Generally speaking, the cooling should take place over a period of hours, preferably 2 hours or less, rather than days, in order to prevent too much crystallisation, although some degree of crystallisation is acceptable, for example 20% or particularly 10%, or less. The gel forms by a phase separation which produces a concentrated polymer-rich phase and a polymer-poor phase. The polymer-rich phase may have only, say, 10% w/w water and hence be glassy at room temperature, even though the whole gel may contain over 90% w/w water. The whole preparation may be dried, if necessary or desirable, at 0°–160° C., preferably 20°–100° C. and more preferably about 60° C. in air or an inert atmosphere, for example nitrogen, or in vacuo in order to give a glassy or more glassy product.

The dry glassy amylose may be melted in the form of a slab or film or may first be powdered or granulated. Such melting is assisted if the Tg is depressed with a suitable diluent such as water. The melted amylose can then be used to coat preparations of active compound.

Alternatively, an aqueous or aqueous alcoholic, for example aqueous butanol, solution of amylose, preferably 1 to 15%, suitably 2 to 10% and advantageously about 2 to 3% w/w, is sprayed directly onto a formulation containing an active compound and allowed to dry in air, in an inert atmosphere, for example nitrogen, or in vacuo to the glassy form. A further variation is for the aqueous solution to be sprayed as described onto a suitable inert support or into a sufficiently large volume of air or inert gas to form a glassy film or glassy particles which are then melted and used to coat the active compound formulation as above.

Generally speaking, the moisture content of the glassy amylose should be as low as possible. Conveniently, therefore, it does not exceed 20% (w/w) and preferably is less than this, for example being no more than 10, 5 or 1% (w/w).

In both the gel-forming and spraying processes, it is possible to include dispersions or solutions of suitable active compounds in the amylose solution itself, so that the resulting glassy form actually contains the drug. It may be particularly advantageous to injection mould an amylose solution containing an active compound to form solid glassy pellets.

The amylose may be prepared from any suitable source although it is preferably prepared from starch, for example cereal starch or tuber starch but particularly starch from pulses, for example smooth-seeded pea starch, conveniently by precipitation from aqueous solution as a complex with an alcohol, for example 1-butanol, methanol, ethanol, propan-1-ol, propan-2-ol, pentanol, 2-methylbutan-2-ol or 2-methylbutan-1-ol as described by Ring et al., Macromolecules, 1985, 18, 182. The alcohol may conveniently then be removed from an aqueous dispersion of that complex by blowing through a suitable heated inert gas, for example nitrogen.

It will be appreciated that the presence of other materials in admixture with the glassy amylose will detract from the selective nature of the degradation of this material as between the stomach and small intestine and the large intestine. It is preferred therefore that the glassy amylose is substantially free (i.e. contains no more than 20% by weight and preferably no more than 10% or 5% by weight) of any material which is susceptible to digestion in the stomach or small intestine. In particular the glassy amylose preferably contains no more than 10% or 5% by weight of amylopectin, for example 1 or 2% or less, and conveniently also of any material containing glucoside linkages of the type found in amylopectin.

Moreover it is preferred that the glassy amylose does not contain hydroxy groups in derivative form and, if any derivatization is present that this is conveniently to an extent of no more than 10% of the hydroxy groups present, in particular no more than 4 or 5% and particularly 1 or 2% or less.

A convenient test for the purity of the amylose is provided by its iodine binding ability in a standard assay procedure such as is described by Banks et al. Starke, 1971, 23, 118. Thus pure, underivativized amylose binds with iodine to a level of about 19.5% w/w (i.e. 19.5±0.5% w/w) whereas the other main starch polysaccharide, amylopectin, binds less than 2.0% w/w and derivativization of the amylose will also reduce this binding ability. Conveniently therefore the amylose used in the present invention binds with iodine to a level of 15.0%±0.5% w/w, or above, preferably to a level of 18.0%±0.5% w/w or above, and particularly to a level of 19.5±0.5% w/w.

The molecular weight of the amylose used in the invention may conveniently be at least 20,000 g/mol (or daltons) and is preferably higher so that it is advantageous to use amylose with a molecular weight of at least 100,000, 200,000, 300,000, 400,000 or 500,000 g/mol depending on the particular circumstances.

Although there is a preference for the use of glassy amylose in the compositions of the present invention it is also possible to use rubbery amylose. In particular, it may be appropriate for reasons of aiding the coating procedure, controlling permeability or otherwise to add a plasticizer to the amylose in the same way as is described hereinafter in relation to the use of plasticizers with the cellulose or acrylic polymer material. This may lead to the formation of amylose which is rubbery rather than glassy at ambient temperature since the plasticizer can depress the Tg of amylose which would otherwise be glassy to some tens of degrees, i.e. 10°, 20°, 30° C., or more, below ambient temperature. Despite the latitude of up to 20° C. above the Tg for the retention of glassy characteristics mentioned hereinbefore the amylose of the composition may well then be rubbery at physiological temperature if not also at ambient temperature. Such compositions containing rubbery amylose are however also of value, particularly when prepared with a water soluble plasticizer since such plasticizers will tend to be leached out in an aqueous environment to produce a porous amylose material. Especially when using an inner coating of amylose and an outer coating of the cellulose or acrylic polymer material, as discussed hereinafter, this may provide a particularly suitable way of achieving a controlled release in the colon.

In another aspect the present invention includes compositions and their uses as described in U.K. Patent Application No. 0212048.9 (published as GB 2220350A) referred to hereinbefore and in its equivalents (Canadian Patent Application 600598, European Patent Application 89305318.1, and PCT Application GB/00581 and the national applications in Denmark, Finland, Japan, Norway and the U.S.A. deriving therefrom) in which the glassy amylose described therein is replaced by rubbery amylose, particularly rubbery amylose prepared using a plasticizer as described above.

The term "active compound" particularly includes any compound useful in human or veterinary medicine in therapy or diagnosis. Therapeutic agents of particular interest have been referred to hereinbefore. In addition to their value in achieving a delayed release of therapeutic agents, particularly in their delivery to the colon as discussed above, the compositions of the invention are also of interest in a diagnostic context, for example in delivering agents such as contrast media to the colon in connection with X-ray and NMR imaging techniques. An alternative diagnostic area lies in the delivery of potentially allergenic foodstuff components to the colon for the diagnosis of allergies.

It will be appreciated that the active compound may be mixed with other carrier materials suitable to its particular use. Thus, particularly for therapeutic use, the active compound will often be mixed with one or more of a bulking agent and a lubricant, for example lactose and magnesium stearate, respectively. Dosages of active compounds for therapeutic use will be as disclosed in the literature, for example in the ABPI Data Sheet Compendium, or may sometimes be less owing to the more efficient delivery of the compound.

One preferred "active compound" is 5-aminosalicylic acid (5-ASA), a drug which is used orally in the treatment of colonic disorders. When free 5-ASA is administered orally, little of the drug reaches the colon as the stomach and small intestine inactivate and/or absorb the drug. The present invention provides a composition comprising 5-ASA which can be administered orally with delayed release of a substantial amount of the active ingredient in the colon. The 5-ASA is preferably provided in the form of spherules, suitably spheronized in admixture with microcrystalline cellulose and a minor proportion of an inorganic binder such as bentonite.

In delayed release compositions according to the invention the amylose is often present as an inner coating to the active compound. Where appropriate, however, the inner coating may not consist entirely of amylose providing the nature and location of the amylose allow appropriate release or exposure of the active compound in the colon. For example, the amylose can provide a "window" in an inert coating, or can provide temporary strength to an otherwise weak inert coating. If desired, a further active compound may be sandwiched between an inner amylose coating and the outer coating of the cellulose or acrylic polymer material. Thus, one can provide for the spaced release of two different drugs. Alternatively it may be appropriate to locate part of the dose of an active compound within an inner coating and part between an inner coating and the outer coating.

The material which is coated with amylose may be a solid, or an aqueous or non-aqueous liquid provided only that it does not degrade the amylose, or at least does not degrade it at an undesirable rate. The amylose need not necessarily be located as a coating in relation to the active compound. Thus, as an alternative to its use as a coating, the amylose may be mixed with the active component, conveniently to produce a matrix throughout which the active component is dispersed. The matrix will then be coated with the cellulose or acrylic polymer material.

However, a particularly preferred form of composition does comprise an active compound coated with amylose, which amylose is further coated with the cellulose or acrylic polymer material. The present invention thus includes a delayed release composition comprising an active compound coated with an inner coating of amorphous amylose and an outer coating of a film forming cellulose or acrylic polymer material.

The release characteristics of the composition may be controlled by variations in the nature of the two coatings. Thus the degree of permeability of the outer coating of the film forming cellulose or acrylic polymer material can be varied to achieve the desired mode of release of the active compound, particularly through variation of the thickness of the coat but also by the use of plasticizers, for example in an amount of 1 to 10% by weight, especially those of a water soluble nature. As regards thickness, a suitable value can be arrived at by routine and non-inventive experimentation but, by way of guidance, it may be stated that an outer coat with a thickness in the range of 5 to 50 $\mu$m is often preferred, especially in the range 20 to 50 $\mu$m, for example about 40 $\mu$m. However, it will be appreciated that, particularly when plasticizers are incorporated into the coat, a wide range of variation of thickness is possible including sometimes thicknesses greater than those just quoted. Examples of suitable plasticizers, particularly in the case of the cellulose materials, are polypropylene, dibutyl phthalate and especially the water soluble materials polyethylene glycol, glycerol and ethyl citrate.

As well as delaying release of at least substantial amounts of the active compound until the composition reaches the colon, the compositions of the present invention also have a role in controlling release of the active compound once the composition reaches the colon. Thus the rate of breakdown of the amylose by the microflora of the colon may be varied through selection of different thicknesses of amylose for the inner coating. Once again a suitable value can be arrived at as described for the outer coating but by way of guidance it may be stated that an inner coating with a thickness in the range of 5 to 50 $\mu$m is often preferred, especially in the range of 20 to 40 $\mu$m, for example about 30 $\mu$m. It is also possible to vary the release in the colon by coating different particles of the active compound with amylose of different thicknesses. Moreover, the physical nature of the amylose may be varied either by drying which has the effect of reducing the pore size and hence permeability of the gel or by adding a fatty or waxy substance such as carnuba wax to retard penetration of water where this is desirable. Both procedures will in turn affect the rate of metabolism of the amylose by the microflora of the colon. It will be appreciated that the delayed release will depend both on the nature of the amylose itself in providing a slow release barrier and its degradation by micro-organisms when it reaches the colon. Thus some controlled release can be effected in the small intestine by suitable control of the amylose employed.

In a further particularly preferred form of composition according to the invention, the amylose is present in admixture with the cellulose or acrylic polymer of the outer coating. When such a mixed outer coating is employed, it has been found preferable to employ from 3 to 5 parts by weight of cellulose or acrylic polymer per one part by weight of amylose, especially a ratio of about 4:1. It will be appreciated that the thickness of the coating and the proportion of the components can be varied to alter the rate of release.

It will be appreciated that regardless of whether one or two coatings are present, control can be exercised over release of the active ingredient with respect to time by varying one or more of the parameters controlling release, e.g. coat thickness, method of coating and ratio of coating ingredients. It is also possible to employ a mixture of, for example, spherules having coatings designed to provide differing release times so as to allow pulsed release of the active ingredient.

The invention therefore also includes the use of a film forming cellulose or acrylic polymer, an active compound and amorphous amylose for the manufacture of a medicament for use in the treatment of a patient by slow and/or delayed systemic release of the active compound.

The composition may be made up in various forms, for example as a powder or compressed as a monolith or formed solid, for example a tablet, which has an outer coating of the cellulose or acrylic polymer material surrounding an amylose/active compound matrix, an active compound surrounded by an inner coating of amylose or an active compound surrounded by a mixed coating of cellulose or acrylic polymer material and amylose. The plasticizers described above can also be of value in stabilizing coatings on formed compositions such as tablets.

Preferred forms of composition may be prepared by spraying a first coating of amylose on to the active compound or a mixture thereof with other materials as described hereinbefore and then a second coating of the cellulose or acrylic polymer material. The concentration of the cellulose or acrylic polymer material in the spraying solution may be similar to that described for amylose but conveniently with an upper limit of about 5% w/w. Alternatively, a mixture of amylose and the cellulose or acrylic polymer is prepared prior to spraying. A conventional spraying machine such as that marketed under the trade name Aeromatic may conveniently be used for this purpose. The coating agent will be applied in a suitable solvent system, for example aqueous butanol as indicated before in the case of the amylose and an organic solvent such as methylene chloride/methanol in the case of the cellulose or acrylic polymer material.

The invention is illustrated by the following Examples.

EXAMPLE 1: Glassy Amylose Preparation

The starch polysaccharide amylose, an essentially linear polymer composed of $\alpha$-1,4-linked D-glucose, was isolated from smooth-seeded pea starch and purified by precipitation from aqueous solution as a complex with n-butanol. The isolated amylose had a weight average molecular weight of 500,000 g/mol. Concentrated aqueous solutions of amylose were regenerated from aqueous dispersions of the complex by removal of the n-butanol in a heated nitrogen stream. A 7% w/w aqueous solution of the amylose was cast as a gel slab $1.1 \times 10^{-3}$ m thick by rapidly quenching the amylose solution, held between glass plates, from 90° C. to 20° C. The gel was removed from the glass plates and allowed to dry overnight at room temperature. The resulting film had a thickness of $6 \times 10^{-5}$ m.

In Vitro Enzyme Digestion

An amylose film prepared as just described was found to be insoluble in aqueous media over the pH range 1-9 at 37° C. The amylose film was also incubated at 37° C. in 0.05M phosphate buffer (pH 6.9) containing 0.04% w/v NaCl with a crystalline pancreatic α-amylase (25 units/mg polysaccharide). After a three day incubation period less than 10% by weight of the film had been solubilised. An alternative digestion employing a mixed amylose/ ethylcellulose (Ethocel) film in a weight ratio of components of 1:4 showed that after 6 hrs. incubation only a minor proportion (about 16%) of the amylose content of the mixture had degraded.

In Vitro Microbial Digestion

An amylose film prepared as just described was incubated at 37° C. with a mixed faecal inoculum of microorganisms under a carbon dioxide atmosphere, the initial density of micro-organisms being $1 \times 10^7$/ml. After 24 hours the film had lost approximately 50% of its weight, and after 48 hours the film had disintegrated.

EXAMPLE 2: Medicament Formation (A) A 3% w/w aqueous solution of amylose, prepared as described in Example 1, was sprayed at a temperature of 90° C. onto a conventional tablet formulation of sulphasalazine comprising 50 mg of sulphasalazine [4-hydroxy-4'-(2-pyridyl-sulphamoyl)-azobenzene-3-carboxylic acid] in admixture with lactose and magnesium stearate and the wet tablet was dried in a heated air stream at 100° C. to a moisture content of 0.2% w/w. A 10% w/w solution of ethyl cellulose 100 (Ethocel) in 50:50 v/v methylene chloride:methanol was then sprayed at ambient temperature onto the amylose coated tablet, the wet tablet being dried as before.

(B) A 3% w/w aqueous solution of amylose, prepared as described in Example 1, was sprayed at a temperature of 90° C. onto a tablet comprising 500 mg of mesalazine (5-aminosalicylic acid) in admixture with lactose and magnesium stearate and the wet tablet was dried in a heated air stream at 100° C. to a moisture content of 0.2% w/w. A 10% w/w solution of ethyl cellulose 100 (Ethocel) in 50:50 v/v methylene chloride:methanol was then sprayed at ambient temperature onto the amylose coated tablet, the wet tablet being dried as before.

(C) A 3% w/w aqueous solution of amylose, prepared as described in Example 1, was sprayed at a temperature of 90° C. onto a tablet comprising 20 mg of either hydrocortisone or prednisolone in admixture with lactose and magnesium stearate and the wet tablet was dried in a heated air stream at 100° C. to a moisture content of 0.2% w/w. A 10% w/w solution of ethyl cellulose 100 (Ethocel) in 50:50 v/v methylene chloride:methanol was then sprayed at ambient temperature onto the amylose coated tablet, the wet tablet being dried as before.

EXAMPLE 3: Release of Active Compound from Compositions

Theophylline was used as a model active compound. Spheres of 1 mm diameter each containing about 80 μg of theophylline were prepared by the process of extrusion/spheronisation from a formulation containing the drug and microcrystalline cellulose (Avicel PH 101). The spheres were then coated with (a) an amylose coating, (b) an ethyl cellulose coating, or (c) an inner coating of amylose and an outer coating of ethyl cellulose.

The coatings were applied using the Aeromatic spray coating system employing a 3% w/w solution of glassy amylose (prepared as described in Example 1) in 10:90 v/v n-butanol:water at 60° C. or a 10% w/w solution of ethyl cellulose 100 (Ethocel) in 50:50 v/v methylene chloride:methanol at ambient temperature. The volume of coating solution used in each case per 50 g of spheres was 10 ml in (a) and (b) and either 10 ml of each solution or 20 ml of each solution in (c). In cases (a) and (b) the spheres were air dried after coating and in case (c) they were air dried after each coating.

The release of the active compound from the spheres was measured after stirring the spheres using a 50 r.p.m. paddle for 5 hours in 0.1 N aqueous hydrochloric acid, phosphate buffer of pH 4.0 or distilled water. The theophylline was measured via its UV absorption peak at 270 nm. The results obtained are shown in the Table 1 from which it will be seen that the two coatings provide a markedly lower level of release of the active compound than the single coating.

TABLE 1

| Coating System | Percentage of active compound in solution | | |
|---|---|---|---|
| | HCl | Phosphate buffer | H$_2$O |
| Amylose | 51.2 | 70.3 | 97.2 |
| Amylose + ethyl celluose (10 ml + 10 ml) | 10.8 | 9.4 | 24.3 |
| Amylose + ethyl cellulose (20 ml + 20 ml) | 4.8 | 4.2 | 4.2 |

EXAMPLE 4: Delayed Release Compositions Including ASA

Further experiments were carried out using 5-aminosalicyclic acid (hereinafter referred to as '5-ASA') as a representative active compound used in the therapy of colonic disorders.

a) Preparation of 5-ASA-Containing Spheres

Microcrystalline cellulose (Avicel pH 101) and bentonite powder were mixed for 5 minutes and purified water was added followed by further mixing for 10 minutes. The final mixture contained 41.40 wt % 5-ASA, 24.15 wt % microcrystalline cellulose, 3.45 wt % bentonite and 30.90 wt % water. The resulting plastic mass was extruded and the extrudate processed in a spheronizer. The resulting spheres were dried in a fluidized bed for 30 minutes at 60° C. and sieved to obtain spheres of 1.40–1.70 mm diameter and a drug level (based on the total weight of the dried spheres) of 60%.

b) Preparation of Coated Spheres

The spheres obtained as in a) above were coated with the different coatings listed in Table 2 below. In each case the spheres (40 g) were coated in a fluidised bed coater (Aeromatic-Strea-1). The coating methods varied dependent on the nature of the polymer used and are given below in Table 2. The coating weights are given as percentages of total weight of the coated spheres. Ratios for the mixtures are by weight.

TABLE 2

| Sample No. | Coating | Layers | Coating Method |
|---|---|---|---|
| 1 | None | | |
| 2 | amylose (2%) + ethylcellulose (org) (4.8%) | separate | A |

TABLE 2-continued

| Sample No. | Coating | Layers | Coating Method |
|---|---|---|---|
| 3. | amylose (0.9%) + ethylcellulose (org) (2.4%) | separate | A |
| 4. | amylose (0.9%) + ethylcellulose (org) (1.2%) | separate | A |
| 5. | amylose (0.9%) + ethylcellulose (org) (0.6%) | separate | A |
| 6. | ethyl cellulose (aqu) (4.8%) | single | B |
| 7. | ethyl cellulose (aqu) (9.6%) | single | B |
| 8. | (1:4) amylose/ethyl cellulose (aqu) (4.8%) | mixture | B |
| 9. | (1:4) amylose/ethyl cellulose (aqu) (9.6%) | mixture | B |
| 10. | (1:4) amylose/(meth)acrylic copolymer (4.8%) | mixture | C |
| 11. | (1:4) amylose/(meth)acrylic copolymer (9.6%) | mixture | C |
| 12. | (1:4) amylose/(meth)acrylic copolymer (14.4%) | mixture | C |
| 13. | amylose (4.8%) | single | A |

Coating Methods

A) Amylose was applied as a single layer or as a first layer from a 3 to 4% aqueous suspension containing 8% butanol with a product bed temperature maintained at 60° C. The ethyl cellulose layer was applied from an organic medium using ethyl cellulose (available as "Ethyl cellulose N50") dissolved in a 50:50 mixture of dichlormethane and methane to obtain a 5% w/w solution with the product temperature kept between 48° and 50° C. at a feeding rate of 0.3-0.4 ml/min. The coated spheres were cured at 60° C. for 1 hour.

B) Ethyl cellulose in aqueous medium was applied directly to a 20% suspension in aqueous ammonia (commercially available, including an added plasticizer, as "Ethocel"). Mixtures of Ethocel and amylose (supplied as in A) above) were prepared by mixing in the ratio of 4:1 with the temperature maintained above 60° C. during the coating process. The coated spheres were dried for 1 hour at 60° C.

C) A (meth)acrylic copolymer dispersion was prepared from a 1:1 mixture of dispersions of Eudragit RL 30D and Eudragit RS 30D which materials are respectively a high permeability and a low permeability copolymer of acrylic and methacrylic esters with low quaternary ammonium content supplied as 30% aqueous dispersions. The mixture of dispersions (10% w/w based on Eudragit solids) was stirred before coating and throughout coating and 10% w/w of polyethylene glycol plasticizer (PEG 300) based on the polymer weight was added. The resulting mixture was combined with amylose (supplied as in A) above) in a ratio of 4:1 amylose/copolymer and preheated to above 60° C. Coating was effected using preheated spheres at a feeding rate of 0.5 ml/min. The spheres were dried for 2 hours at 40° C.

c) Dissolution of Coatings

The release of 5-ASA from the spheres was measured using 300 mg. spheres (180 mg. 5-ASA) and 900 ml of dissolution fluid at 37° C. at an agitation speed of 100 rpm. The dissolution fluids used were water, 0.1N HCl (pH 1.2) and phosphate buffer pH 7.2. Samples were analysed for 5-ASA content by spectrometry after predetermined time intervals. The results are summarized for 3 hours and 6 hours in Table 3 below.

TABLE 3

| | 5-ASA in solution (%) | | | | | |
|---|---|---|---|---|---|---|
| | Water | | HCl | | Phosphate buffer | |
| Sample | 3 hr. | 6 hr. | 3 hr. | 6 hr. | 3 hr. | 6 hr. |
| 1. | 82.4 | 100 | 100 | 100 | 95.8 | 97.8 |
| 2. | 0 | 0 | | | | |
| 3. | 0 | 0 | | | | |
| 4. | 0 | 4 | | | | |
| 5. | 10.4 | 17.8 | 24.8 | 44.3 | 13.9 | 21.8 |
| 6. | 3.1 | 3.8 | | | | |
| 7. | 2.6 | 3.6 | 0 | 0 | 0 | 1.0 |
| 8. | 1.8 | 4.0 | 2.3 | 8.2 | 1.3 | 2.8 |
| 9. | 3.1 | 3.3 | 0 | 1.4 | 0 | 0 |
| 10. | 13.6 | 25.2 | 46.9 | 81.2 | 35.7 | 52.5 |
| 11. | 5.5 | 13.3 | | | | |
| 12. | 7.8 | 9.3 | | | | |
| 13. | 71.9 | 89.9 | 75.6 | 100 | 57.8 | 68.9 | d) In Vitro Microbial Digestion

The coated spheres as described in Table 2 were subjected to microbial digestion as follows. The sample spheres were introduced into a batch culture system at a concentration of 0.7% by weight of spherules per batch. The system contained 5% w/v faecal slurry preserved in anaerobic phosphate buffer 0.1M pH 7.0, with argon employed as the anaerobic headspace gas phase. The fermenters were incubated at 37° C. and samples removed at time intervals up to 48 hours, centrifuged, and analysed using HPLC to determine the released 5-ASA content. The results are shown in Table 4.

TABLE 4

| | Concentration of 5-ASA mg/ml in solution | | | | | |
|---|---|---|---|---|---|---|
| Sample No. | 4 | 8 | 12 | 24 | 48 | (HOURS) |
| 1. | 0.690 | 1.410 | 1.990 | 2.910 | 4.300 | |
| 2. | 0.014 | 0.035 | 0.015 | 0.070 | 0.065 | |
| 3. | — | 0.010 | 0.020 | 0.069 | 0.147 | |
| 4. | 0.006 | 0.080 | 0.135 | 0.380 | 1.700 | |
| 5. | 0.061 | 0.660 | 1.180 | — | 4.580 | |
| 6. | — | 0.011 | 0.015 | 0.053 | 0.200 | |
| 7. | — | — | — | 0.003 | 0.004 | |
| 8. | — | — | — | 0.011 | 0.046 | |
| 9. | — | — | — | 0.007 | 0.026 | |
| 10. | 0.127 | 0.360 | 0.600 | 1.020 | 1.660 | |
| 11. | 0.128 | 0.260 | 0.450 | 1.130 | 2.080 | |
| 12. | 0.034 | 0.240 | 0.380 | 1.000 | 2.230 | |

We claim:

1. A delayed release composition comprising an active compound and amorphous amylose, having an outer coating comprising a film forming cellulose or acrylic polymer material in an amount sufficient to control the rate of release of the active compound.

2. A delayed release composition according to claim 1 comprising an active compound in admixture with amorphous amylose, the mixture being coated with a film forming cellulose or acrylic polymer material.

3. A delayed release composition comprising an active compound coated with an inner coating of amorphous amylose and an outer coating of a film forming cellulose or acrylic polymer material.

4. A delayed release composition comprising an active compound coated with a mixed coating comprising amorphous amylose and a film forming cellulose or acrylic polymer material.

5. A pharmaceutical composition in the form of a delayed release composition according to claim 1 wherein the active compound is a compound of use in human or veterinary medicine in therapy or diagnosis.

6. A composition according to claim 1, in which the active compound is a medicament for treatment of a disease of the colon or an agent for diagnosis of a disease of the colon.

7. A composition according to claim 6, in which the active compound is 5-aminosalicylic acid.

8. A composition according to claim 7, in which the active compound has been spheronized together with a binder comprising microcrystalline cellulose and a clay.

9. A composition according to claim 1, in which the amorphous amylose is glassy amylose.

10. A composition according to claim 1, in which the film forming material is a cellulose material.

11. A composition according to claim 10, in which the material is an ethyl cellulose.

12. A composition according to claim 1, in which the film forming material is an acrylate/methacrylate copolymer.

* * * * *